(12) United States Patent  
Shapiro

(10) Patent No.: US 8,376,933 B2  
(45) Date of Patent: Feb. 19, 2013

(54) ENDOSCOPIC TOOL FEEDING MODULE

(76) Inventor: Alan D. Shapiro, Potomac Falls, VA (US)

( * ) Notice: Subject to any disclaimer, the term of this patent is extended or adjusted under 35 U.S.C. 154(b) by 330 days.

(21) Appl. No.: 12/825,862

(22) Filed: Jun. 29, 2010

(65) Prior Publication Data

US 2011/0319708 A1 Dec. 29, 2011

(51) Int. Cl.
A61B 1/00 (2006.01)
(52) U.S. Cl. .......................... 600/106; 600/104
(58) Field of Classification Search .......... None
See application file for complete search history.

(56) References Cited

U.S. PATENT DOCUMENTS

| | | | |
|---|---|---|---|
| 6,358,199 B1 * | 3/2002 | Pauker et al. ............ | 600/114 |
| 6,872,178 B2 * | 3/2005 | Weinberg ................ | 600/114 |
| 7,524,284 B2 | 4/2009 | Murakami et al. | |
| 7,582,055 B2 | 9/2009 | Komiya et al. | |
| 2003/0176770 A1 * | 9/2003 | Merril et al. ............ | 600/118 |
| 2008/0039685 A1 * | 2/2008 | Komiya et al. .......... | 600/106 |
| 2010/0152538 A1 * | 6/2010 | Gleason et al. .......... | 600/117 |

* cited by examiner

Primary Examiner — Matthew J Kasztejna  
Assistant Examiner — Alexandra Newton  
(74) Attorney, Agent, or Firm — MH2 Technology Law Group, LLP

(57) ABSTRACT

A tool feeding module for an endoscopic apparatus is disclosed. The module includes a housing removably connected to the endoscopic apparatus. A channel is formed within the housing, the channel having an inlet, an outlet, and discrete sections between the inlet and outlet, the channel configured to receive a tool therethrough. An insertion length selection switch is configured to select a length of the tool fed through the channel. A feed mechanism is aligned with and positioned between the discrete sections, the feed mechanism configured to advance and retract the tool through the channel. A tool advancement switch is formed proximate the inlet, contact with the tool advancement switch by the tool automatically activating an advance of the tool into the channel via the feed mechanism. Actuation of the manual retraction switch mounted on the housing of the device activates retraction of the tool out of the channel via the feed mechanism.

20 Claims, 5 Drawing Sheets

ENDOSCOPIC TOOL FEEDING MODULE

FIELD OF THE INVENTION

This invention relates generally to an endoscopy treatment device, more particularly, to a tool advancement/retraction module thereof.

BACKGROUND OF THE INVENTION

Advancement and retraction of biopsy forceps and related endoscopy tools is currently performed on a manual basis, and requires time consuming physical effort by the operator and assistant to accomplish. In other devices, advancement and retraction of tools is remotely monitored, allowing little or no direct control by the physician performing a procedure. Further, in some devices, advancement and retraction is remotely manipulated by, for example, a technician, with separate direction from, for example, the physician, at the site, requiring constant communication to the technician, who is unable to directly view the procedure.

It would, therefore, be desirable to provide a device operable to enable advancement/retraction of endoscopic tools, which is directly operated and monitored at the examination site, and which can be automatically operated by a single individual.

SUMMARY OF THE INVENTION

According to various embodiments, the present teachings include a tool feeding module for an endoscopic apparatus. The tool feeding module can include a housing removably connected to the endoscopic apparatus; a channel formed within the housing, the channel comprising an inlet, an outlet, and discrete sections between the inlet and outlet, the channel configured to receive a tool therethrough; an insertion length selection switch configured to select a length of the tool fed through the channel; a feed mechanism aligned with and positioned between the discrete sections, the feed mechanism configured to advance and retract the tool through the channel; a tool advancement switch formed proximate the inlet, contact with the tool advancement switch by the tool automatically activating an advance of the tool into the channel via the feed mechanism; and a housing mounted retraction switch that manually activates the retraction of the tool out of the channel via the feed mechanism.

According to various embodiments, the present teachings include a method of using a tool feeding module for an endoscopic apparatus. The method can include connecting the module to an endoscopic apparatus; selecting a tool feed length via an insertion length selection switch; inserting an endoscopic tool into a discrete substantially fluid tight channel interior of the module, the channel comprising an insertion end and an outlet end and configured to confine the tool relative to a remainder of the interior of the module; insertion of the tool automatically activating an advancement switch positioned proximate the channel inlet, the advancement switch initiating advancement of the tool in a direction of the outlet end via a feed mechanism; and manually actuating the retraction switch, the switch initiating the retraction of the tool in a direction of the inlet end via the feed mechanism.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the invention, and together with the description, serve to explain the principles of the invention.

It should be noted that some details of the figures have been simplified and are drawn to facilitate understanding of the inventive embodiments rather than to maintain strict structural accuracy, detail, and scale.

DESCRIPTION OF THE EMBODIMENTS

Reference will now be made in detail to the present embodiments (exemplary embodiments) of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration, specific exemplary embodiments in which the invention may be practiced. These embodiments are described in sufficient detail to enable those skilled in the art to practice the invention, and it is to be understood that other embodiments may be utilized and that changes may be made without departing from the scope of the invention. The following description is, therefore, merely exemplary.

As used herein, the term "endoscope" refers to a medical device having a long, thin, flexible (or rigid) tube which typically includes a light source and a video camera. Images of the inside of a patient's body can be seen on a display screen. Endoscopy is a minimally invasive diagnostic and/or therapeutic medical procedure. It is used to examine the interior surfaces of an organ or tissue. The endoscope can also be used for enabling biopsies and retrieving foreign objects.

Figure 1A:
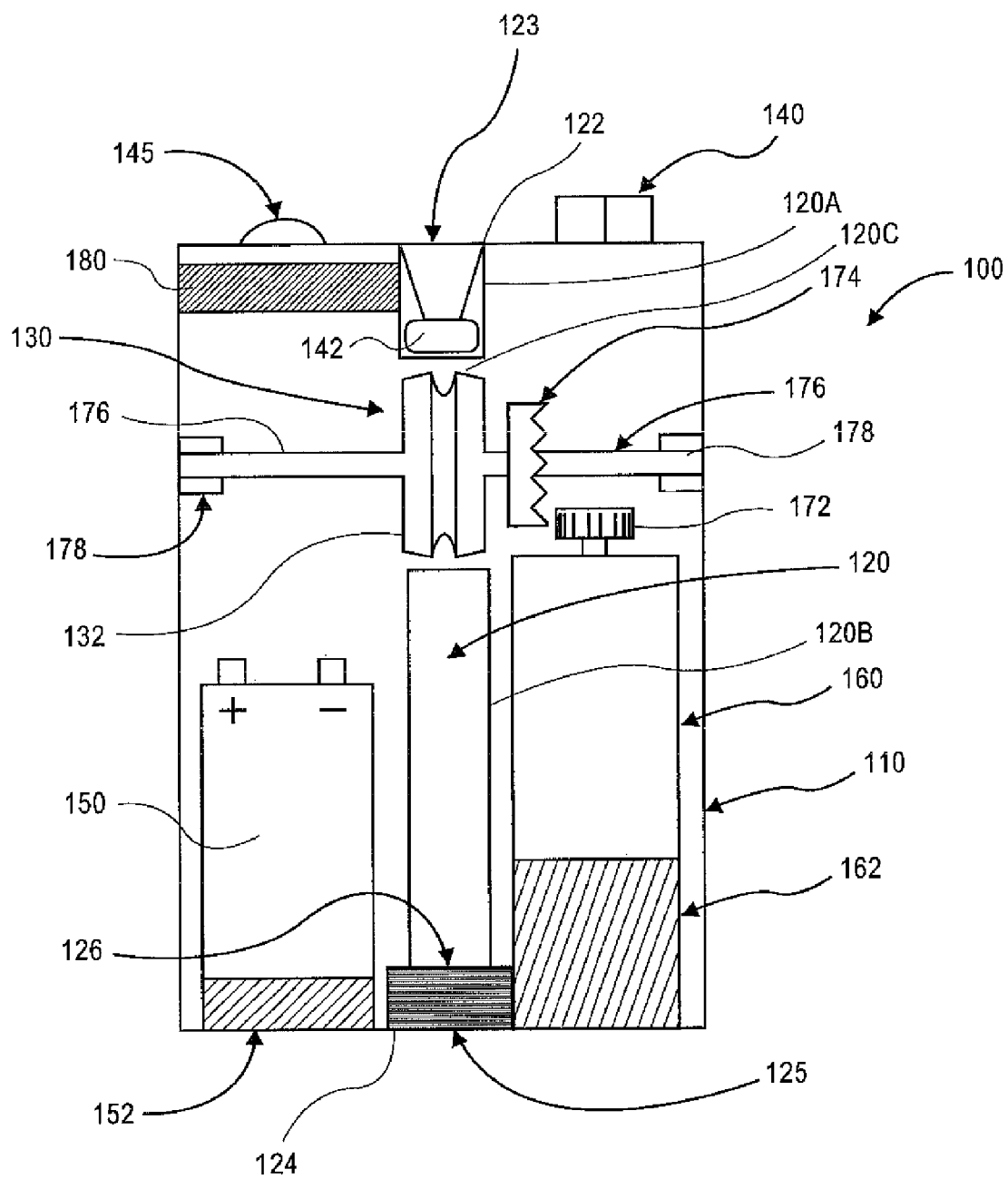
FIG. 1A is a side sectional view of a tool feeding module for an endoscopic apparatus in accordance with the present teachings.
Figure 1B:
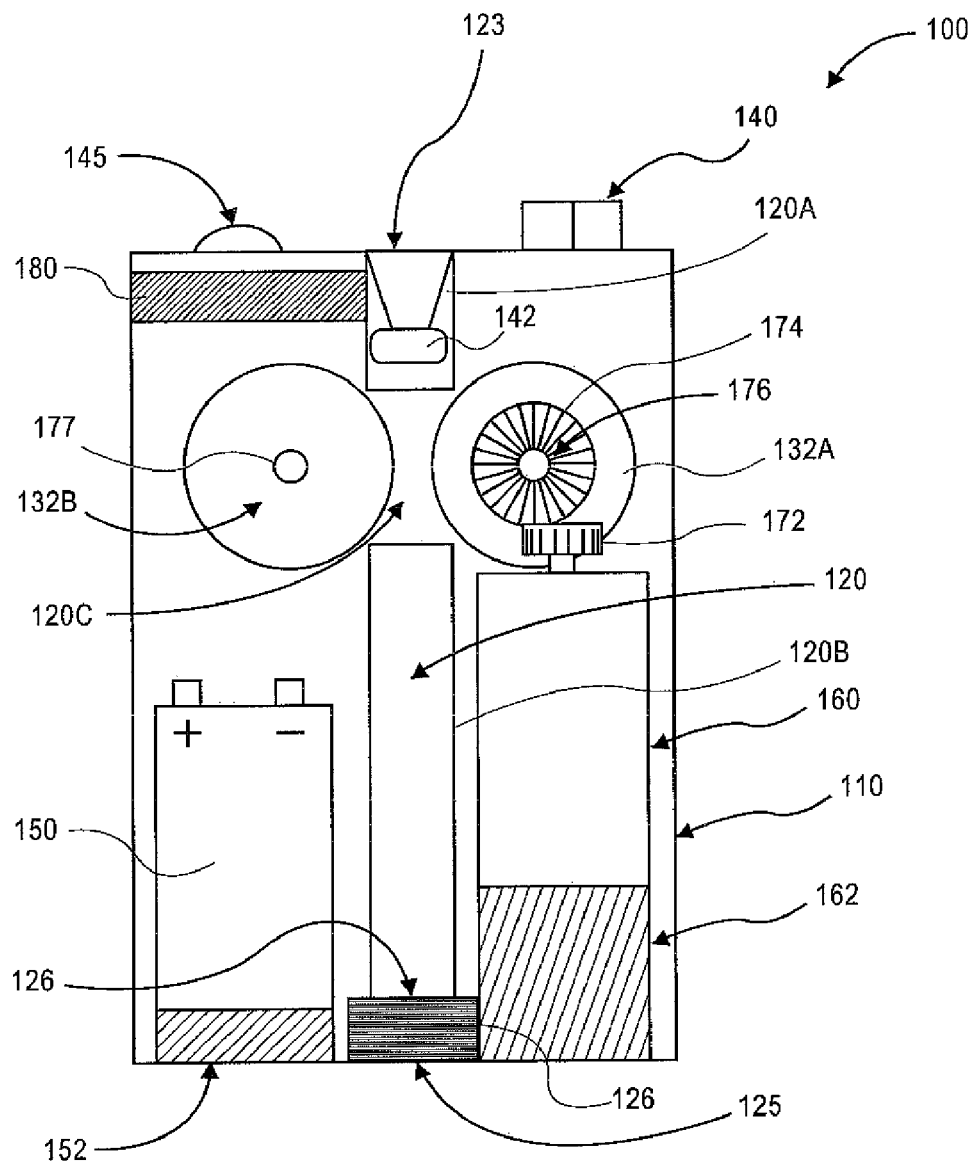
FIG. 1B is a side view of the tool feeding module for an endoscopic apparatus, taken from a 90 degree angle relative to FIG. 1A, in accordance with the present teachings.
Figure 1C:
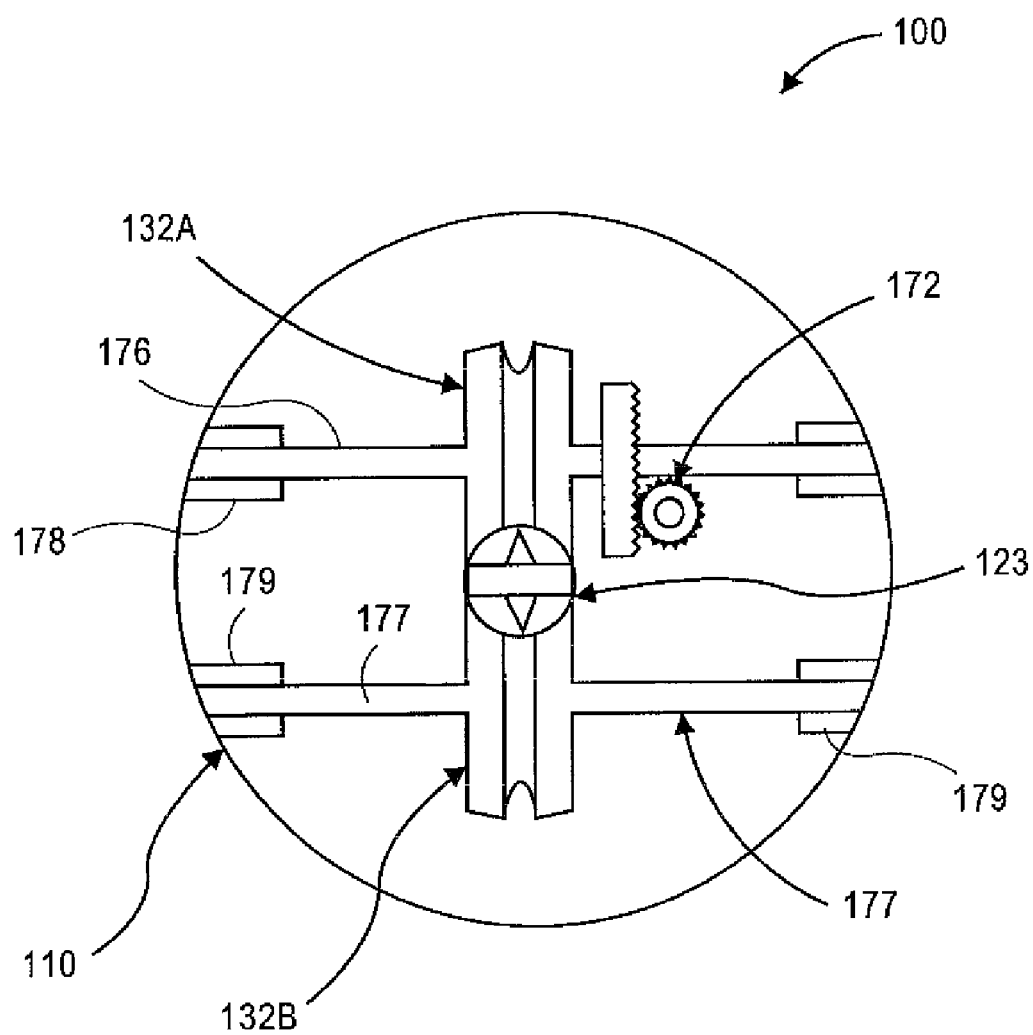
FIG. 1C is a top cutaway view of the tool feeding module for an endoscopic apparatus, in accordance with the present teachings.

FIGS. 1A through 1C depict an exemplary tool feeding module 100 for an endoscopic apparatus in accordance with the present teachings. It should be readily apparent to one of ordinary skill in the art that the module 100 depicted in FIGS. 1A through 1C represents a generalized schematic illustration and that other components can be added or existing components can be removed or modified. It will be appreciated that the module 100 and its components are not necessarily shown to scale, but are instead selectively enlarged to illustrate certain features for purposes of description.

As shown in FIGS. 1A through 1C, the tool feeding module 100 can include a housing 110, a channel 120 formed within the housing, the channel 120 having an inlet 122, an outlet 124, and discrete sections 120a, 120b between the inlet 122 and outlet 124, with the channel 120 configured to receive an endoscopic tool 102 (see FIG. 4) therethrough. The module 100 further includes a feed mechanism 130 aligned with and positioned between the discrete sections 120a, 120b. The feed mechanism 130 can include feed rollers, the feed rollers 132 configured to advance and retract the tool through the channel 120. An insertion length selection switch 140 can be formed on the housing 110, the insertion length selection switch 140 configured to interactively select a feed length of the tool 102 through the channel 120 via the feed rollers 132. A pressure switch 142 can directly or indirectly activate the feed rollers 132 to advance the endoscopic tool 102 through channel 120 according to a length set by the insertion length selection switch 140. A power supply 150, drive motor 160, and motion transmitting gears 172 and 174 can be provided internal to the housing 110 for effecting operation of the module components. For example, activation of the pressure switch 142 by insertion and pressure from the endoscopic tool 102 in turn enables the drive motor 160 and motion transmitting gears 172,174 to rotate the feed rollers 132 and advance (or retract) the endoscopic tool 102 through the channel 120. The power supply 150 can be supported on a battery mount 152 or similar structure, and the drive motor 160 can be supported on a motor mount 162 or similar structure, within the housing 110.

The housing 110 can be of a shape and material to contain each of the components identified above. It will be appreciated that the housing 110 can be of a size to mate with an existing endoscopic apparatus 200, and preferably of a size to fit within a user's hand for ease of operability and attachment to the endoscopic apparatus, without interfering with operation of control wheels of the existing endoscopic apparatus 200.

The channel 120 can be formed through the housing 110. In embodiments, the channel 120 can include the inlet 122 at one end and the outlet 124 at an opposing end of the channel. The channel 120 can be formed along or substantially parallel to a longitudinal axis of the housing 110, with the appreciation that the module 100 can be operable at an angle to which it is mounted to the endoscopic apparatus 200. The inlet 122 of the channel 120 can be formed substantially flush with an outer surface of the housing 110, and the outlet 124 can be formed substantially flush with an opposing outer surface of the housing 110. The inlet 122 can include an insertion port 123. The insertion port 123 is the location at which the endoscopic tool 102 can enter the channel 120. The insertion port 123 can include a resilient stopper having an opening therein. The opening can allow advancement and retraction of tool 102 while maintaining an hermetic seal around the tool 102. Further, the insertion port 123 can allow the attachment of a typically used syringe, enabling fluid irrigation through the channel 120 of the module 100, and continuing through the biopsy channel of the endoscopic apparatus 200. The insertion port 123 can include the pressure switch 142 which can act in conjunction with the insertion length selection switch 140. The pressure switch 142 initiates forward movement of the feed rollers 132.

The outlet 124 can further include a threaded surface 125. Threads can be formed on an inner surface of the channel 120 or on an outer surface of the channel according to device parameters. The threaded surface 125 can enable the module 100 to be connected to the endoscopic apparatus 200 at the outlet 124 of the channel 120, providing a secure connection between the module 100 and the endoscopic apparatus 200. An o-ring seal 126 can be provided at or adjacent to the outlet 124 of the channel 120. The o-ring seal 126 can be in a region between the threaded portion at the outlet 124 and the remainder of the channel 120. As depicted, the channel 120 can include discrete sections 120a, 120b. The discrete sections 120a, 120b can have a gap 120c therebetween; however, the discrete sections remain longitudinally aligned regardless of the size of the gap 120c.

In various embodiments, the gap 120c can be sized to receive the feed mechanism 130 therebetween. The feed mechanism 130 can include a pair of rotatable wheels 132, with one wheel configured as a drive wheel 132a and the remaining wheel configured as an idler wheel 132b. The wheels 132 can be configured to include a grooved surface 133. Within the housing 110, the wheels 132 can be aligned such that the grooved surfaces 133 are facing each other, the grooved surface 133 shaped to grip an endoscopic tool 200. The wheels 132 can be spaced to accommodate the endoscopic tool 200 therebetween. More specifically, the wheels 132 can be spaced such that the endoscopic tool 200 can be gripped by opposed grooved surfaces 133, without slippage of the tool 102. The grooved surface 133 of the wheel 132 can include a surface material suitable to increase friction and prevent slippage between the tool 102 and the grooved surface 133 of the wheel 132. For example, a synthetic rubber coating can be formed on a part or an entirety of the inner grooved portion 133 of the wheel 132 to ensure adequate grip on the tool 102 during insertion and retraction.

The insertion length selection switch 140 can interactively select a feed length of the tool 102 through the channel 120 via the feed mechanism 130. The insertion length selection switch 140 can be configured as, for example, a rotary switch. The insertion length selection switch 140 can set a distance that the tool 102 will advance when the pressure switch 142 is actuated. The length of the tool 102 advanced by the feed mechanism 130 can be selected by the insertion length selection switch 140 based upon the total length of the endoscope utilized by the operator. Full control of the tool 102 can be achieved by the operator of the module's housing mounted controls. Because of the direct control available at the module 100, remote assistance or actuation in connection with advancement of the tool 102 can be eliminated.

In addition to the insertion length selection switch 140, a manual retraction actuator 145 can be configured on the housing 110 of the module 100. The manual retraction actuator 145 can include a push button switch. Upon actuation of the manual retraction actuator 145, rotation of the wheels 132 of the feed mechanism 130 can be reversed, enabling retraction of the tool 102 from the channel 120. Upon completion of use of a tool 102 during a procedure, the tool 102 can be completely retracted with the manual retraction actuator 145.

The power supply 150 can supply power to an electronic control device 180 within the housing 110. The electronic control device 180 can be connected to each of the insertion length selection switch 140, the pressure switch 142, the manual retraction actuator 145 and the drive motor 160 of the module 100. The drive motor 160 can respond to actuation of either of the pressure switch 142 or the manual retraction actuator 145, enabling rotation of the feed mechanism 130 in either of an advancement or retraction mode, respectively. The power supply 150 can supply power to the drive motor 160 and the electronic control device 180.

More specifically, the motion transmitting gears can include a pinion gear 172, a drive gear 174, and a drive shaft 176 passing through a center axis of the drive wheel 132a. The drive shaft 176 can be rotatably supported within the housing 110 by bearings 178. The bearings 178 can be mounted to an inner wall surface of the housing 110, so as to rotatably support opposing ends of the drive shaft 176, as known in the art. As shown in the top plan view of FIG. 1C, the idler wheel 132b can be mounted to an idler shaft 177, the idler shaft 177 rotatably supported at opposing ends thereof, via bearings 179, to an inner wall of the housing 110. Upon actuation of the drive motor 160 by either of the pressure switch 142 or the retraction actuator 145, the pinion gear 172 rotates to actuate the drive gear 174. Rotation of the drive gear 174 correspondingly rotates drive shaft 176, thereby rotating the drive wheel 132a. It will be appreciated that rotation of the drive wheel 132a in an inward direction will cause the idler wheel 132b to rotate as well about the idler shaft 177, and the tool 102 can be advanced into the channel 120 between grooved surfaces 133 for use with the endoscopic device 200. Likewise, rotation of the drive wheel 132a in an outward direction will cause the idler wheel 132b to rotate in an outward direction as well, and the tool 102 can be retracted from the channel 120.

Figure 2:
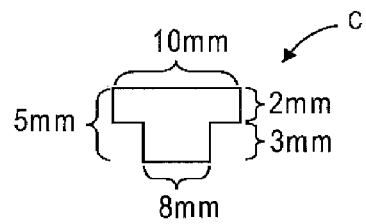
FIG. 2 is a side view (not to scale) depicting a conventional endoscope biopsy port connector.

FIG. 2 is a side view depicting a conventional endoscope biopsy port connector C. As depicted, the conventional connector C is configured as a flanged lug having an opening therethrough (not shown). The connector C is permanently mounted on the endoscope. The lug portion of the connector has a diameter of about 8 mm and a height of about 3 mm. The flange portion of the connector has a diameter of about 10 mm, and a height of about 2 mm, with an overall height of the connector being about 5 mm. It will be appreciated that the flanged lug connector of FIG. 2 is not drawn to scale.

Figure 3:
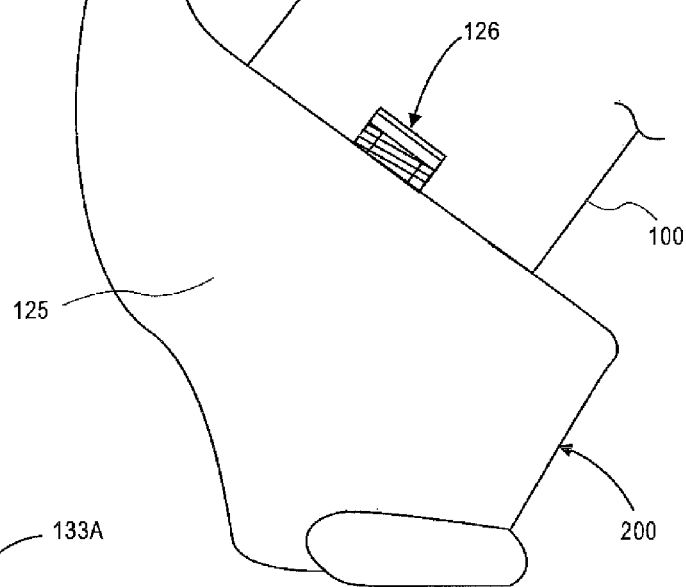
FIG. 3 is a side view of the exemplary module connected to an endoscopic apparatus in accordance with the present teachings.

FIG. 3 is a partial side view of the exemplary module 100 detailing the connection between the module 100 and the endoscopic apparatus 200 in accordance with the present teachings. It should be readily apparent to one of ordinary skill in the art that the connection depicted in FIG. 3 represents a generalized schematic illustration and that other components can be added or existing components can be removed or modified.

As previously described, the outlet 124 of channel 120 can include a threaded surface 125, the threaded surface mating with the flange of the biopsy port connector C of the endoscopic apparatus 200. The connection between the endoscopic apparatus 200 and the module 100 at the outlet 124 can be secured via the o-ring seal 126.

Figure 4:
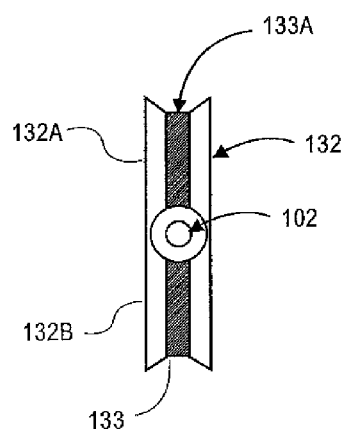
FIG. 4 is a top plan view of a portion of an exemplary drive mechanism relative to a tool channel in accordance with the present teachings.

FIG. 4 is a top plan view detailing the exemplary feed mechanism 130 relative to a tool channel in accordance with the present teachings. It should be readily apparent to one of ordinary skill in the art that the feed mechanism 130 depicted in FIG. 4 represents a generalized schematic illustration and that other components can be added or existing components can be removed or modified.

From FIG. 4, the relationship of the wheels 132 of the feed mechanism 130 is depicted relative to the tool 102 being fed therethrough. Although some clearance is seen between the grooved surfaces 133 of the wheels 132 and the tool 102, it will be appreciated that there can be a much closer tolerance between these components in order for the wheels 132 to advance and retract the tool 102 therebetween. In addition, the grooved surfaces 133 can include the treated surface 133a, of for example, a rubber or similar frictional surfacing. The rubber coating 133a can be in part or all of the grooved surface 133 and on one or both grooved surfaces. For example, the rubber coating 133a can be formed in the deepest recess of the grooved surface 133, on only the grooved surface proximate the outer ends of the parabola defining the grooved surface, or over an entirety of the grooved surface. Each of the drive roller 132a and the idler roller 132b can be coated differently or the same.

Figure 5:
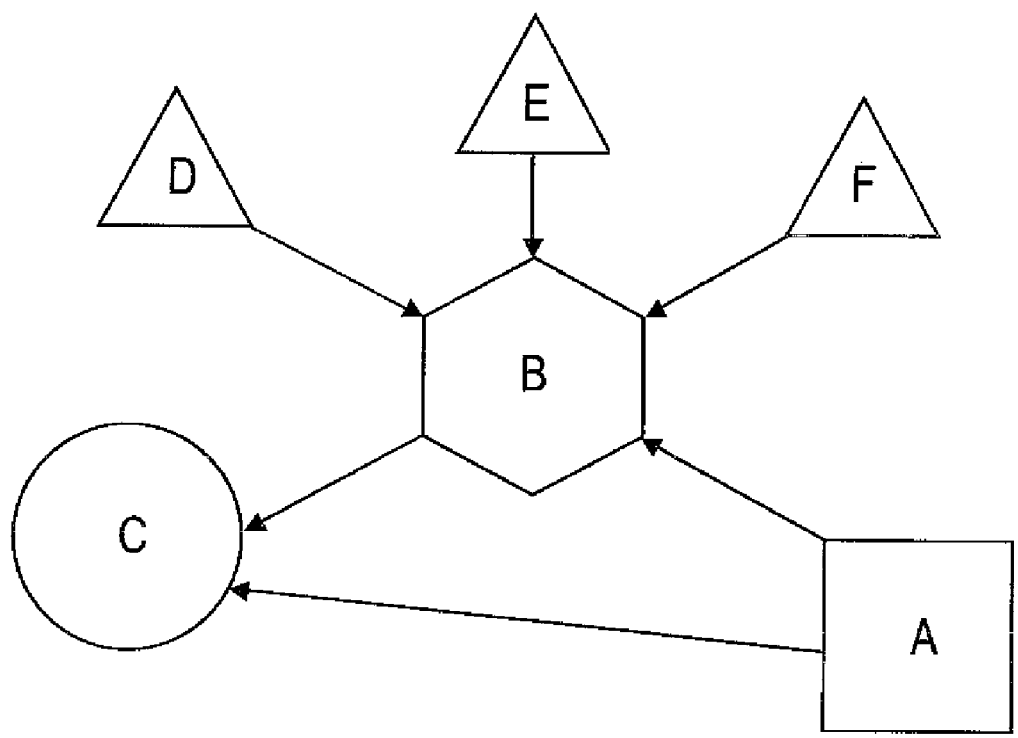
FIG. 5 is a diagram depicting control and system schematics of the exemplary module in accordance with the present teachings.

FIG. 5 is a diagram depicting control and system schematics of the exemplary module in accordance with the present teachings. It should be readily apparent to one of ordinary skill in the art that FIG. 5 represents a generalized schematic illustration and that other components can be added or existing components can be removed or modified.

In FIG. 5, the electronic control module B is depicted at the center of the diagram, and each of the power source A, motor C, insertion length selector switch D, insertion port pressure switch E, and manual retraction actuator F are depicted surrounding the control module B. Arrows indicate the direction of control current to and from the electronic control module. The control electronics can determine a length of a tool, (e.g. forceps) inserted and retracted, as well as the speed of each insertion and retraction.

As viewed in FIG. 5, the insertion length selection switch D, insertion port pressure switch E, and manual retraction actuator F, each selectively inform the control module B of their operation. The power source A can supply power to the control module B. The control module B can initiate operation of the motor C. The motor C in turn operates the motion transmitting gears 170 of FIG. 1 and subsequently the feed mechanism 130, ultimately in accordance with the selective input from the insertion length selection switch D, insertion port pressure switch E, and manual retraction actuator F.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A tool feeding module for an endoscopic apparatus, the module comprising:
    a housing removably connected to the endoscopic apparatus;
    a channel formed within the housing, the channel comprising an inlet, an outlet, and discrete sections between the inlet and outlet, the channel configured to receive a tool therethrough;
    an insertion length selection switch configured to select a length of the tool fed through the channel, wherein the insertion length selection switch comprises a manual adjustment member disposed on the housing;
    a feed mechanism aligned with and positioned between the discrete sections, the feed mechanism configured to advance and retract the tool through the channel; and
    a tool advancement switch formed proximate the inlet, wherein the tool advancement switch is configured to be tripped when contacted by the tool, and, in response, causes the feed mechanism to advance the tool into the channel until the pressure exerted by the tool is removed from the tool advancement switch, the length is reached, or both.

2. The device of claim 1, further comprising a refraction actuator configured to initiate removal of the tool via the feed mechanism, wherein the retraction actuator is disposed on the housing and is configured to be manually actuated.

3. The device of claim 1, wherein the channel comprises two of the discrete sections.

4. The device of claim 1, wherein the feed mechanism comprises a pair of grooved wheels.

5. The device of claim 4, wherein the pair of grooved wheels comprise a drive wheel and a guide wheel.

6. The device of claim 4, wherein the pair of grooved wheels are configured to grip the tool.

7. The device of claim 6, wherein the pair of grooved wheels comprise a friction enhancing surface.

8. The device of claim 1, wherein the tool advancement switch comprises a pressure switch.

9. The device of claim 1, wherein the channel further comprises a gap disposed between two of the discrete sections, the gap being configured to house at least a portion of the feed mechanism, wherein the channel defines a substantially fluid tight passage through said housing.

10. The device of claim 1, further comprising a power supply coupled with the feed mechanism, to power the feed mechanism, wherein the power supply comprises a battery.

11. The device of claim 1, further comprising a drive motor to drive the feed mechanism, wherein the drive motor comprises an electric motor.

12. The device of claim 1, wherein the feed mechanism further comprises:
    one or more drive wheels configured to turn to advance the endoscopic tool; and
    a gear actuated shaft directly connected to the one or more drive wheels.

13. The device of claim 1, wherein the tool comprises one of a biopsy forceps, diagnostic, and therapeutic devices.

14. The device of claim 1, wherein the module is connected to the endoscopic apparatus at a connection end of the channel.

15. The device of claim 14, wherein the connection end is threaded for removable attachment to the endoscopic apparatus.

16. The device of claim 1, wherein the housing is configured to hermetically seal with the endoscopic tool at least proximal the inlet of the channel.

17. The device of claim 1, wherein the manual adjustment member is a rotary knob.

18. A method of using a tool feeding module for an endoscopic apparatus, the method comprising:
    connecting the module to an endoscopic apparatus;
    selecting a tool feeding length by manually adjusting an insertion length selection switch disposed on an exterior of a housing of the module; and
    inserting an endoscopic tool into a substantially fluid tight channel defined in an interior of the module, the channel comprising an insertion end and an outlet end and configured to confine the tool relative to a remainder of the interior of the module,
    wherein when the tool is inserted, the tool contacts an advancement switch positioned proximate the channel inlet and trips the advancement switch, wherein, when tripped, the advancement switch initiates advancement of the tool in a direction of the outlet end via a feed mechanism until the pressure exerted by the tool is removed from the tool advancement switch, the tool feed length is reached, or both.

19. The method of claim 18, further comprising selectively activating a retraction actuator of the module, wherein selectively activating the retraction actuator initiates retraction of the tool in a direction of the inlet end via the feed mechanism.

20. The method of claim 18, wherein tool feed length is selected according to a length of the endoscopic apparatus being utilized.

* * * * *